United States Patent [19]

Spallholz

[11] 4,166,820
[45] Sep. 4, 1979

[54] SELENIUM COMPOUNDS

[76] Inventor: Julian E. Spallholz, 17441 Mashie Cir., Huntington Beach, Calif. 92647

[21] Appl. No.: 821,646

[22] Filed: Aug. 4, 1977

[51] Int. Cl.$^2$ .................. C07D 207/46; C07D 421/12
[52] U.S. Cl. .............................. 260/326.4; 546/207; 546/248; 546/222; 546/238; 546/243; 260/326 A; 260/239 R; 560/105; 560/142
[58] Field of Search .................. 260/326.22, 326.4

[56] References Cited

U.S. PATENT DOCUMENTS 3,317,559  5/1967  Anderson .................. 260/326.4
3,541,084  11/1970  Hagitani et al. .................. 260/326.4

OTHER PUBLICATIONS

Bolton et al.; Biochem. 9, vol. 133, pp. 529-539 (1973).
New England Nuclear; Bolton-Hunter Reagent [$^{125}$I].

Primary Examiner—Donald G. Daus
Assistant Examiner—Mary Lee
Attorney, Agent, or Firm—Fulwider, Patton, Rieber, Lee & Utecht

[57] ABSTRACT

Selenium compounds, and a method of their preparation, are disclosed which have a structure that renders the compounds useful in immunoassays or in competitive protein binding assays wherein either radio-labeled selenium compounds or nonradioactive selenium compounds are used respectively, with radiologic or fluorometric analysis. One class of these compounds have the generalized structural formula of:

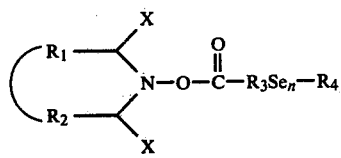

wherein:
X is hydrogen or oxo;
$R_1$ and $R_2$, together, are ethylene, trimethylene, or 5,6-phenylene;
$R_3$ is alkylene of 1 to 6 carbons;
$R_4$ is alkyl or isoalkyl of 1 to 6 carbons, phenyl or benzyl; or
$R_3$ and $R_4$ together are 1,2,3-propanetriyl;

and n is 1 or 2. The compounds in the aforementioned structure are N-pyrrolidine derivatives wherein $R_1$ and $R_2$ together are ethylene; N-succinimdyl derivatives when $R_1$ and $R_2$ together are ethylene and the X groups are oxo groups; N-phthalimidyl derivatives when $R_1$ and $R_2$ are 5,6-phenylene and the X groups are oxo; and N-piperidyl compounds when $R_1$ and $R_2$ together are trimethylene.

Another class of these compounds has the generic formula:

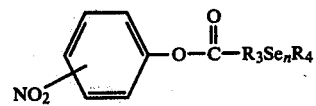

wherein: $R_3$, $R_4$ and n are as previously defined.

19 Claims, No Drawings

SELENIUM COMPOUNDS

BACKGROUND OF THE INVENTION

1. Field of the Invention:

This invention relates to certain selenium compounds, a method for their preparation and, in particular, to selenium compounds having applications in competitive protein binding assays such as immunoassays.

2. Brief Statement of the Prior Art:

Competitive protein binding assay, e.g., immunoassay, is a recent development wherein known quantities of labeled and unlabeled antigen binding reactants, such as a hormone, are admixed with a protein, e.g., antibody, and the resultant product is analyzed for the concentration of bound or unbound labeled antigen or hapten to determine reactant concentrations, reaction kinetics and the like. The procedure has been widely used in an application known as radioimmunoassay to measure biological concentrations of materials in blood and urine such as digitalis glycosides, morphine, vitamins, enzymes, other proteins, polypeptides and viruses.

A material which is widely used in radioimmunoassay is the Bolton-Hunter reagent. This material is the N-hydroxysuccinimide ester of iodinated p-hydroxyphenylpropionic acid. The radioactive isotope of iodine ($^{125}I$) is used in the radioassay. In typical applications with this material a standard preparation of unlabeled hormone and plasma, serum or urine sample to be assayed are admixed with identical quantities of hormone labeled with the above-mentioned reagent and specific antibody. The antibody competes with labeled and unlabeled hormones in a competitive binding reaction. The resultant mixture is treated to separate the free from the bound hormone and the separated portions are then analyzed for radioactivity to determine the ratio between the bound and unbound hormone for the purpose of hormone quantitation.

The aforementioned Bolton-Hunter reagent has a number of disadvantages which limit its applications. The half-like of the iodine ($^{125}I$) is 60 days, and the reagent, therefore, requires iodination shortly prior to its use. The iodine is bound to a bulky hydroxyphenyl group which limits, to some extent, the reactivity with antibody and reagent labeled antigens and haptens. The bulky organic portion of the compound also renders the compound somewhat hydrophobic and this also limits its immunologic reactivity, specificity, and applications. Finally, the Bolton-Hunter reagent requires the employment of an unstable radioactive iodine tracer, ($^{125}I$), and it is most desirable to provide a small molecular tracer reagent that will bind to antigens, haptens and antibodies and permit simple, nonradioactive analysis such as fluoroassays.

BRIEF DESCRIPTION OF THE INVENTION:

I have now conceived and successfully synthesized selenium compounds which have a high reactivity for proteins, polypeptides and other compounds to permit bonding of the selenium compound to haptens, antibodies and antigens and provide a facile selenium assay useful in competitive protein binding applications such as immunoassays. The use of the selenium compounds for these applications provides the investigator with a choice of using radioactive tracer techniques with the radioactive selenium isotopes, e.g., ($^{75}Se$) or the fluorometric assay analysis with any of the selenium isotopes, particularly the common nonradioactive selenium isotope mixture ($^{79}Se$).

The compounds of the invention have the generic structural formula of:

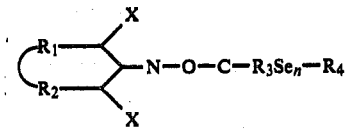

wherein:

X is hydrogen or oxo;

$R_1$ and $R_2$, together, are ethylene, trimethylene, or 5,6-phenylene;

$R_3$ is alkylene of 1 to 6 carbons;

$R_4$ is alkyl or isoalkyl of 1 to 6 carbons, phenyl or benzyl; or $R_3$ and $R_4$ together are 1,2,3-propanetriyl;

and n is 1 or 2.

The subject compounds are prepared by the reaction of a seleno-aliphatic acid and the appropriate N-hydroxy substituted heterocyclic amines or nitrophenol, with dicyclohexylcarbodimide in tetrahydrofuran to form a crude reaction product from which the compounds can be purified by filtration, extraction and crystallization. The seleno-substituted aliphatic acids are prepared by the reaction of diselenoaliphatic acids with methyliodide and sodium formaldehyde sulphoxylate from which the seleno-aliphatic acids are recovered by ether extraction. The diseleno-aliphatic acids are prepared by the reaction of a bromine substituted aliphatic acid with selenium in the presence of a basic solution of sodium formaldehyde sulphoxylate.

DESCRIPTION OF PREFERRED EMBODIMENTS:

This invention comprises selenium compounds and methods for their preparation according to the following structural formulae:

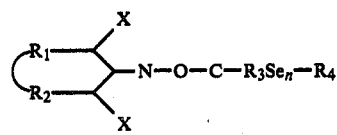

wherein:

X is hydrogen or oxo;

$R_1$ and $R_2$, together, are ethylene, trimethylene, or 5,6-phenylene;

$R_3$ is alkylene of 1 to 6 carbons;

$R_4$ is alkyl or isoalkyl of 1 to 6 carbons, phenyl or benzyl; or $R_3$ and $R_4$ together are 1,2,3-propanetriyl;

and n is 1 or 2.

Depending on the identity of the $R_1$ and $R_2$ grouping and the ensuing heterocyclic compound, a series of N-substituted heterocyclic compounds are prepared. When $R_1$ and $R_2$ together are ethylene and the X groups are hydrogen, the subject compounds are pyrrolidinyl derivatives, or, when the X groups oxo, succinimidyl derivatives. When the $R_1$ and $R_2$ grouping is 3,4-phenylene, the subject compounds are benzopyrrolidinyl derivatives which, when the X groups are oxo, are phthalimidyl derivatives.

In the aforementioned structural formulae, it is preferred that the R₃ and R₄ groups be of limited carbon chain length. Typically R₃ is alkylene of 1 to 6 carbons, e.g., methylene, dimethylene, trimethylene, tetramethylene, pentamethylene and hexamethylene. Of these, methylene and dimethylene are most preferred to limit the molecular weight, size and hydrophobic character of the compound. Similarly, R₄ is alkyl or isoalkyl of 1 to 6 carbons such as methyl or ethyl, propyl, isopropyl, butyl, isobutyl, amyl, hexyl, isohexyl, etc. R₄ can also be phenyl or benzyl.

The selenium of these compounds can be a radioactive isotope ($^{75}$Se) or can be a non-radioactive isotope, typically that of a weighted isotope mixture ($^{79}$Se). This is a mixture of the following selenium isotopes:

| Isotope | Weight Percent |
|---------|----------------|
| 80      | 48             |
| 78      | 24             |
| 76      | 10             |
| 82      | 9              |
| 77      | 8              |
| 74      | 1              |

The aforementioned compounds will typically be monoseleno wherein n=1. It is, however, possible to incorporate greater quantities of selenium in the compounds by using diselenium compounds, thereby improving the sensitivity of the assay in which the compound is used as a tracer. This can be achieved by use of a compound wherein R₃ and R₄ together are 1,2,3-propanetriyl thereby forming the following heterocyclic diseleno five member ring structure:

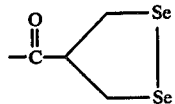

The subject compounds can be prepared from commercially available reactants using, in general, three synthesis steps. In the first synthesis step, selenium is reacted with an aliphatic acid substituted with bromine at the desired selenium substitution carbon. The reaction is performed with strongly alkaline aqueous sodium formaldehyde sulphoxylate to prepare a diselenoaliphatic acid that is recovered from the aqueous preparation by acidification. The precipitate can be filtered, washed, and dissolved and crystallized in a solvent such as methanol.

In the second step of the preparation, the diselenoaliphatic acid is treated with methyliodide in the presence of aqueous basic sodium formaldehyde sulphoxylate from which the monoseleno aliphatic acid is recovered by acidification, extraction and fractional distillation.

The third step of the preparation comprises the reaction of an N-hydroxy substituted heterocyclic of the appropriate structure or a nitrophenol with the seleno aliphatic acid in the presence of dicyclohexylcarbodimide in tetrahydrofuran. Solid reaction precipitates are filtered and the filtrate can be evaporated, dissolved, using a solvent such as methanol from which the desired product is precipitated and purified by elution through a column of an adsorbent such as silica gel. Thereafter the desired product can be obtained by crystallization from the solvent.

The following example will illustrate the method of synthesis and results obtained in a typical preparation:

EXAMPLE 1

Diseleno-dipropionic acid is prepared by the addition of 6 grams sodium hydroxide and 7.7 grams sodium formaldehyde sulphoxylate to 200 milliliters of water. The solution is maintained at 0° C. with continuous stirring and 7.9 grams of selenium powder are dissolved therein, forming a red-colored solution of sodium diselenide. This and the following procedure is followed when using either radioactive or non-radioactive selenium isotopes. Thereafter, 15.3 grams of 3-bromopropionic acid dissolved in 50 ml water and sufficient potassium carbonate to provide a pH of 8.0 is slowly added to the sodium diselenide solution. The mixture is stirred overnight at 22° C. and diselenopropionic acid having a characteristic yellow color is formed. The resultant solution is filtered and cooled in an ice bath. Concentrated hydrochloric acid is added to adjust the pH to 2.0, resulting in precipitation of the acid. The precipitate is filtered, washed with water, and dissolved in methanol from which it is crystallized to obtain 10.5 grams of a purified diseleno-dipropionic acid with a melting point of 130°–132° C.

An amount of 7.6 grams of the diseleno-dipropionic acid is dissolved in 100 ml of 4 N ammonium hydroxide. The solution is stirred and maintained at 0° C. and 3.9 grams sodium formaldehyde sulphoxylate is added, whereupon, the characteristic yellow color of the diseleno-dipropionic acid slowly disappears. Approximately 30 minutes later, 8.5 grams of methyliodide dissolved in 5 ml of methanol is added to the solution and the mixture is stirred overnight at a temperature of between 0 and 5° C. The solution is thereafter acidified to a pH of 2.0 with 2 N sulphuric acid and then extracted in three stages with 200 ml. diethylether in each extraction stage. The ether extracts are combined and washed with water, dried with anhydrous sodium sulphate and the ether solvent is evaporated. The residue is fractionally distilled to collect 3-methylselenopropionic acid distilling at 105°–107° C. under 1 mm mercury pressure. A total of 5.1 grams of product are obtained.

A quantity of 3.34 grams of the 3-methylselenopropionic acid and 2.3 grams of N-hydroxysuccinimide are dissolved in 25 ml of dry tetrahydrofuran stirring continuously in an acetone-dry ice bath. Dicyclohexylcarbodimide in an amount of 4.95 grams is added while stirring for two hours and the mixture is then stirred overnight at a temperature of from 0 to 5° C. Thereafter, 0.5 ml acidic acid and 40 ml ethylacetate are added to the reaction mixture. The mixture is stirred for an additional hour and then filtered to remove N-N'-dicyclohexylurea. The filtered solid is washed with ethyl acetate, the washings are combined with the filtrate, and the solvent is evaporated to obtain a residue which is dissolved in 100 ml dry methanol. The methanol solution is heated to boiling, a small amount of charcoal is added and the mixture is filtered on a celite bed. The filtrate is then cooled in an acetone-dry ice bath to precipitate N-succinimidyl-3-(methylseleno) propionate. The product is filtered, dissolved in ethyl acetate and passed through a silica gel column, eluded with 300 ml of additional ethyl acetate. The elute is washed with water and dried over anhydrous sodium sulphate. The ethyl acetate solvent is evaporated and the product is dissolved in dry methanol from which it is crystallized. The product obtained has a melting point of 56° C. and an elemental analysis of 41.26% C., 5.19% H, and 5.11% N, corresponding to the theoretical of 41.0% C, 5.13% H, and 4.79% N.

Using the aforementioned procedure, the compounds set forth in the following table are obtained having the melting points and elemental analysis indicated in the table:

TABLE 1

| Compound | Melting Point °C. | Molecular Formula | Calculated Analysis C Weight % | H Weight % | (Determined Analysis) N Weight % |
|---|---|---|---|---|---|
| N-succinimidyl-mrthylseleno acetate | 105 | $C_7H_9O_4NSe$ | 33.6 (33.75) | 3.6 (3.63) | 5.6 (5.42) |
| N-succinimidyl-ethylseleno acetate | — | $C_8H_{11}O_4NSe$ | 36.36 (36.8) | 4.13 (4.23) | 5.30 (5.45) |
| N-succinimidyl-3-(methylseleno)-propionate | 65 | $C_8H_{11}O_4NSe$ | 36.36 (36.9) | 4.13 (4.39) | 5.30 (5.53) |
| N-succinimidyl-3-(ethylseleno)-propionate | 85 | $C_9H_{13}O_4NSe$ | 38.84 (39.28) | 4.67 (4.76) | 5.03 (5.25) |
| N-succinimidyl-3-(isopropylseleno)-propionate | 83 | $C_{10}H_{15}O_4NSe$ | 41.0 (41.28) | 4.79 (5.11) | |
| | | | 5.13 (5.19) | | |
| N-succinimidyl-3-(n-propylseleno)-propionate | 56 | $C_{10}H_{15}O_4NSe$ | 41.0 (41.26) | 5.13 (5.19) | 4.79 (5.11) |
| N-succinimidyl-3-(n-butylseleno)-propionte | 48 | $C_{11}H_{17}O_4NSe$ | 43.13 (43.24) | 5.55 (5.71) | 4.57 (4.50) |
| N-succinimidyl-4-(ethylseleno)-butyrate | — | $C_{10}H_{15}O_4NSe$ | 41.0 (41.09) | 5.13 (5.41) | 4.79 (4.77) |
| N-phthalimidyl-methylseleno acetate | 118 | $C_{11}H_9O_4NSe$ | 44.29 (44.32) | 3.02 (3.02) | 4.69 (4.71) |
| N-phthalimidyl-ethylseleno acetate | 45 | $C_{12}H_{11}O_4NSe$ | 46.15 (46.68) | 3.52 (3.66) | 4.49 (4.57) |
| N-phthaliidyl-3-(ethylseleno)-propionate | 60 | $C_{13}H_{13}O_4NSe$ | 47.85 (48.09) | 3.98 (4.10) | 4.29 (4.40) |
| N-phthalimidyl-3-(n-propylseleno)-propionate | 48 | $C_{14}H_{15}O_4NSe$ | 49.41 (49.50) | 4.41 (4.36) | 4.11 (4.30) |
| N-phthalimidyl-3-(n-butylseleno)-propionate | 40 | $C_{15}H_{17}O_4NSe$ | 50.85 (50.99) | 4.80 (4.68) | 3.95 (4.05) |
| N-phthalimidyl-3-(benzylseleno)-propionate | 101 | $C_{18}H_{15}O_4NSe$ | 55.67 (55.69) | 3.87 (3.86) | 3.61 (3.55) |
| N-phthalimidyl-4-(ethylseleno)-butyrate | 48 | $C_{14}H_{15}O_4NSe$ | 49.41 (49.38) | 4.41 (4.43) | 4.11 (4.17) |
| N-piperidyl-3-(ethylseleno)-propionte | — | $C_{10}H_{19}O_2NSe$ | 45.45 (46.5) | 7.19 (7.24) | 5.30 (5.45) |
| p-Nitrophenyl-ethylseleno acetate | 37 | $C_{10}H_{11}O_4NSe$ | 41.66 (41.96) | 3.82 (3.86) | 4.86 (4.61) |
| p-Nitrophenyl-3-(ethylseleno)-propionate | 25 | $C_{11}H_{13}O_4NSe$ | 43.71 (43.79) | 4.30 (4.30) | 4.63 (5.75) |
| p-Nitrophenyl-3-(n-propylseleno)-propionate | 48 | $C_{12}H_{15}O_4NSe$ | 45.57 (45.77) | 4.75 (4.78) | 4.43 (3.80) |
| p-Nitrophenyl-3-(n-butylseleno)-propionate | — | $C_{13}H_{17}O_4NSe$ | 47.27 (47.70) | 5.15 (5.28) | 4.24 (4.30) |
| p-Nitrophenyl-3-(benzylseleno)-propionate | 40 | $C_{16}H_{15}O_4NSe$ | 52.75 (52.77) | 4.12 (4.30) | 3.85 (3.76) |

EXAMPLE 2

This example illustrates the reactivity of the selenium compounds of the invention:

A quantity of 5 milligrams of cytochrome c in 10 milliliters of 0.1 Molar sodium borate buffer at pH of 8.5 is added to a sufficient quantity of the selenium compound of the invention to provide from 3 to 4 molecular weights selenium compound per molecular weight of cytochrome c. Thereafter, 0.5 ml. of 0.2 Molar glycine buffered to pH of 8.5 is added to react with unreacted selenium compound, and the reaction products are separated by dialysis.

Samples of the product are dialyzed against multiple changes of 0.1 Normal NaOH followed by exhaustive dialysis against dilute (0.5 or 0.25 Molar) phosphate buffer at pH of 7.0 Sodium selenite is also added to samples of cytochrome c and dialyzed.

After dialysis samples of cytochrome c of 1 mg are analyzed for selenium by the method described by Cummins et al, "An Improved Method for Determination of Selenium in Biological Material", Anal. Chem. 37: 430-431 (1965).

The selenium compounds exhibit high reactivity; the N-succinimidyl-3-(methylseleno) propioniate reacts rapidly at 0° C., acylating approximately 6 of the 19 available amino groups of cytochrome c within a few minutes as apparent from the data tabulated in the following:

| Reaction Time (Min. at 0° C.) | Moles Se/Mole Cytochrome c |
|---|---|
| 0 | 0 |
| 1 | 6 |
| 15 | 6 |
| 30 | 6 |
| 45 | 6 |

The reaction was only slightly concentration dependent, suggesting that the 13 non-acylated amino groups were unavailable for acylation.

The reaction samples can also be assayed by a fluorimetric method. In this method, the samples are digested with a mixture of nitric and perchloric acids to obtain the selenium in the $+6$ oxidation state, then reduced with stannous chloride to the $+4$ oxidation state. The samples are then admixed with 1,2-diaminonaphthalene or 1,2,10,11-tetra-aminobenzidene, which form a selenium complex that can be processed in an automated fluorimetric method of analysis as reported by Brown et al in *Analytica Chimica Acta* 89, p. 29-35 (1977), "An Automated Fluorimetric Method For The Determination Of Nanogram Quantities Of Selenium".

The same reaction procedure is followed to obtain reaction samples of cytochrome c acylated by the radioactive isotope ($^{75}$Se) N-succinimidyl-3-(methylseleno)-propionate. The samples are worked up by the same dialysis method and are assayed in a gamma well scintillation counter to reveal similar reaction activity with cytochrome c.

The invention has been described with reference to the presently preferred embodiments. It is not intended that the invention be unduly limited by this disclosure of the presently preferred embodiment of the invention. Instead, it is intended that the invention be defined by the products, reagents, steps, and their obvious equivalents, set forth in the following claims

What is claimed is:

1. Selenium compounds of the formula:

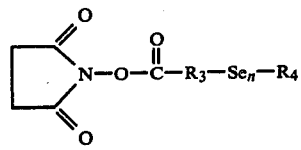

wherein:
R₃ is alkylene of 1 to 6 carbons;
R₄ is alkyl or isoalkyl of 1 to 6 carbons, phenyl or benzyl; or
R₃ and R₄ together are 1, 2, 3-propanetriyl;
and n is 1 or 2.

2. The compounds of claim 1 wherein n is one.

3. N-succinimidyl acetate derivatives of claim 2 wherein R₃ is methylene.

4. The N-succinimidyl acetate derivative of claim 3 wherein R₄ is methyl.

5. The N-succinimidyl acetate derivative of claim 3 wherein R₄ is ethyl.

6. N-succinimidyl propionate derivatives of claim 2 wherein R₃ is dimethylene.

7. The N-succinimidyl propionate derivative of claim 6 wherein R₄ is methyl.

8. The N-succinimidyl propionate derivative of claim 6 wherein R₄ is ethyl.

9. The N-succinimidyl propionate derivative of claim 6 wherein R₄ is isopropyl.

10. The N-succinimidyl propionate derivative of claim 6 wherein R₄ is n-propyl.

11. The N-succinimidyl propionate derivative of claim 6 wherein R₄ is n-butyl.

12. N-succinimidyl butyrate derivatives of claim 3 wherein R₃ is trimethylene.

13. The N-succinimidyl butyrate derivative of claim 12 wherein R₄ is ethyl.

14. Diseleno compounds of claim 1 wherein R₃ and R₄ are 1, 2, 3-propanetriyl and n is 2, forming the radical:

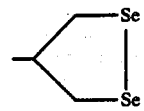

15. The succinimidyl compounds of claim 1 wherein said selenium is isotope 75.

16. The succinimidyl acetate compounds of claim 2 wherein said selenium is isotope 75.

17. The succinimidyl acetate compounds of claim 5 wherein said selenium is isotope 75.

18. The succinimidyl propionate compounds of claim 6 wherein said selenium is isotope 75.

19. The succinimidyl propionate compounds of claim 8 wherein said selenium is isotope 75.

* * * * *